US009476078B2

(12) United States Patent
Tan

(10) Patent No.: US 9,476,078 B2
(45) Date of Patent: Oct. 25, 2016

(54) TAILORED MULTI-SITE COMBINATORIAL ASSEMBLY

(75) Inventor: Xuqiu Tan, San Diego, CA (US)

(73) Assignee: BASF Enzymes LLC, San Diego, CA (US)

( * ) Notice: Subject to any disclaimer, the term of this patent is extended or adjusted under 35 U.S.C. 154(b) by 572 days.

(21) Appl. No.: 12/671,231

(22) PCT Filed: Jul. 31, 2008

(86) PCT No.: PCT/US2008/071771

§ 371 (c)(1), (2), (4) Date: May 13, 2010

(87) PCT Pub. No.: WO2009/018449

PCT Pub. Date: Feb. 5, 2009

(65) Prior Publication Data

US 2010/0216192 A1 Aug. 26, 2010

Related U.S. Application Data

(60) Provisional application No. 60/953,171, filed on Jul. 31, 2007.

(51) Int. Cl.
*C12P 19/34* (2006.01)
*C12N 15/10* (2006.01)

(52) U.S. Cl.
CPC ............. *C12P 19/34* (2013.01); *C12N 15/102* (2013.01); *C12N 15/1024* (2013.01)

(58) Field of Classification Search
CPC ............................ C12N 15/102; C12Q 1/686
See application file for complete search history.

(56) References Cited

U.S. PATENT DOCUMENTS 4,683,195 A 7/1987 Mullis
4,683,202 A 7/1987 Mullis
5,354,670 A 10/1994 Nickoloff
5,830,696 A 11/1998 Short
5,932,419 A 8/1999 Bauer
5,935,830 A 8/1999 Meyer
5,965,408 A 10/1999 Short
6,171,820 B1 1/2001 Short
6,238,884 B1 5/2001 Short
6,335,160 B1 1/2002 Patten
6,335,179 B1 1/2002 Short
6,352,842 B1 3/2002 Short
6,358,709 B1 3/2002 Short
6,361,974 B1 3/2002 Short
6,391,548 B1 5/2002 Bauer
6,440,668 B1 8/2002 Short
6,479,258 B1 11/2002 Short
6,489,145 B1 12/2002 Short
6,537,776 B1 3/2003 Short
6,562,594 B1 5/2003 Short
6,605,449 B1 8/2003 Short
6,635,449 B2 10/2003 Short
6,673,610 B2 1/2004 Miyawaki
6,696,275 B2 2/2004 Short
6,709,841 B2 3/2004 Short
6,713,279 B1 3/2004 Short
6,713,281 B2 3/2004 Short
6,713,282 B2 3/2004 Short
6,713,285 B2 3/2004 Bauer
6,740,506 B2 5/2004 Short
6,764,835 B2 7/2004 Short
6,773,900 B2 8/2004 Short et al.
6,878,531 B1 4/2005 Seyfang
6,939,689 B2 9/2005 Short
6,949,383 B2 9/2005 Tanabe
7,078,389 B2 7/2006 Glazer
7,132,265 B2 11/2006 Bauer
7,176,004 B2 2/2007 Bauer
7,202,086 B2 4/2007 Delcourt
2002/0028443 A1 3/2002 Short
2002/0083488 A1 6/2002 Miyawaki
2002/0086322 A1 7/2002 Yu et al.

(Continued)

OTHER PUBLICATIONS

Dumon, C. et al., "Engineering Hyperthermostability into a GH11 Xylanase is Mediated by Subtle Changes to Protein Structure", Journal of Biological Chemistry, American Society for Biochemistry and Molecular Biology Inc. US, vol. 283, No. 33, pp. 22557-22564, Aug. 15, 2008.

(Continued)

*Primary Examiner* — David Thomas
(74) *Attorney, Agent, or Firm* — BASF; Brian W. Siddons

(57) ABSTRACT

The present invention provides a novel method of producing a plurality of modified polynucleotides having different combinations of various mutations at multiple sites by a tailored multi-site combinatorial assembly, comprising adding at least two or at least three primers to a double stranded template polynucleotide in a single reaction mixture, wherein the primers are not overlapping, and wherein each of the primers comprise at least one mutation different from the other primers, wherein at least one primer is a forward primer that can anneal to a minus strand of the template and at least one primer is a reverse primer that can anneal to a plus strand of the template, and subjecting the reaction mixture to a polymerase extension reaction to yield a plurality of extended modified polynucleotides from the at least three primers. The method can be performed without employing a ligation step prior to transforming the extended modified polynucleotides into a cell. The plurality of extended modified polynucleotides can be treated with an enzyme for destroying the template polynucleotide prior to transforming in to the cell.

33 Claims, 15 Drawing Sheets

(56) References Cited

U.S. PATENT DOCUMENTS

| | | | |
|---|---|---|---|
| 2002/0182734 | A1 | 12/2002 | Diaz-Torres |
| 2003/0077613 | A1 | 4/2003 | Soderlind |
| 2003/0113759 | A1 | 6/2003 | Short |
| 2003/0129709 | A1 | 7/2003 | Makarova |
| 2003/0194807 | A1 | 10/2003 | Crea |
| 2003/0207287 | A1 | 11/2003 | Short |
| 2003/0224492 | A1 | 12/2003 | Young |
| 2004/0002057 | A1 | 1/2004 | Kang |
| 2004/0023327 | A1 | 2/2004 | Short |
| 2004/0248131 | A1 | 12/2004 | Rudel |
| 2004/0248143 | A1 | 12/2004 | Short |
| 2004/0253729 | A1 | 12/2004 | Bauer |
| 2005/0100985 | A1 | 5/2005 | Short |
| 2005/0142658 | A1 | 6/2005 | Short |
| 2005/0186622 | A1 | 8/2005 | Stemmer |
| 2005/0208515 | A1 | 9/2005 | Short |
| 2006/0051748 | A1 | 3/2006 | Hogrefe |
| 2006/0134624 | A1 | 6/2006 | Salerno |
| 2006/0199222 | A1 | 9/2006 | Diaz-Torres |
| 2006/0223066 | A1 | 10/2006 | Lao et al. |
| 2006/0228786 | A1 | 10/2006 | Salerno |
| 2007/0026438 | A1 | 2/2007 | Smith et al. |

OTHER PUBLICATIONS

EP08782567.5—Extended EP Search Report—Aug. 25, 2010.

Levy, M. S., Nucleic Acids Research (2000) 28(12): e57.

Neidhardt John et al., “Different Amino Acid Substitutions at the Same Position in Rhodopsin Lead to Distinct Phenotypes”, IOVS, vol. 47, No. 4, pp. 1630-1635, Apr. 2006.

Kirsch—Nucleic Acids Research (1998)—26—7—1848-1850.

Hogrefe—BioTechniques (2002) 33—5—1158-1165.

Evolution – GSSM™ (2)

Six Mutations Assembly 47 136 159 226 233 349

Figure 5.

Six Mutations Assembly

Four Mutations Assembly

Four Mutations Assembly

Four Mutations Assembly

Three Mutations Assembly 47 136 159

Figure 11.

Three Mutations Assembly

TAILORED MULTI-SITE COMBINATORIAL ASSEMBLY

CROSS REFERENCE TO RELATED APPLICATIONS

This application claims priority to U.S. Provisional Application Ser. No. 60/953,171, filed Jul. 31, 2007, the content of which is incorporated herein by reference.

BACKGROUND OF THE INVENTION

1. Field of the Invention

The present invention relates generally to a method of a tailored multi-site combinatorial assembly ("TMCA") as a method of producing a plurality of progeny polynucleotides and making specific changes to a gene and reassembling mutations or changes at multiple sites. The mutations or changes are designed and synthesized on short oligonucleotides. The oligonucleotides are annealed to a template DNA comprising the wild type gene. A DNA polymerase is used to amplify the whole DNA. The resulting amplified DNA is recovered from a host. The advantages of this method are speed, technical simplicity, and ability to control the assembly.

2. Description of the Background

Published methods of making changes to a gene use, for example, an error-prone PCR, Invitrogen's Gene Tailor site-directed Mutagenesis Kit™, Stratagene's QuickChange Mutagenesis Kit™, overlap PCR and PCR-based ligation/recombination. A survey of the known methods reveals that these methods tend to face a primary difficulty of generating a mutation and/or modification at a single site/neighborhood region and/or are laborious for making modifications at multiple regions.

U.S. Pat. No. 7,202,086 ("the '086 patent") claims a process for mutagenesis using at least 5 oligonucleotides overlapping or not and dsDNA (plasmid) to generate a library of mutated genes, wherein each mutation is present on average in less then ⅕ of the genes in the library. The '086 patent describes that the disclosed invention is different from that of the prior art because the '086 patent requires controlling the frequency of mutations to avoid "excess of mutations" in one DNA molecule (col. 5, lines 28-45). It is desired to get mutants each containing one mutation. In order to achieve this goal, the ratio between the quantity of each mutant oligonucleotide and the quantity of a template must be between 0.01-100 (col. 5, lines 28-45). This feature is distinguished from that of the prior art, wherein using several oligonucleotides simultaneously leads to the level of incorporation of each primer of more than 75% (col. 5, lines 28-45). The '086 patent requires controlling the frequency of mutations to avoid "excess of mutations" in one DNA molecule and to generate mutants each containing one mutation.

U.S. Pat. No. 7,132,265 ("the '265 patent") and U.S. patent publication 2003/0064516 claim a method of introducing mutations into a single stranded DNA ("ssDNA") molecule comprising annealing a primer, synthesizing a DNA strand, and digesting the DNA molecule. The TCMA method uses double stranded DNA ("dsDNA") as the template. The '265 patent makes a clear distinction between using ssDNA and dsDNA as the starting substrate for mutagenesis protocols (see, e.g., col. 6, lines 45-55).

U.S. published application 2003/0194807 are directed to a library wherein mutants of a protein comprise a single predetermined amino acid in one or more positions in a defined region, wherein the defined region is at least three amino acids. Only a single change at a location is permitted, i.e., excludes degenerative changes at a particular amino acid position.

Each of U.S. published applications 2006/0051748; 2006/0134624; 2004/0248131; and 2002/0083488; and U.S. Pat. Nos. 6,673,610; 6,335,160; and 5,354,670 require ligating synthesized DNA to produce progeny circular DNA with the mutations.

Further, U.S. published application 2006/0051748 requires using a flap endonuclease and annealing all primers to the same DNA strand. U.S. published application 2006/0134624 requires using two primers consecutively (i.e., not in one reaction). In U.S. published application 2004/0248131, primers are annealed to two strands, wherein the primers have to comprise 2-4 complementary base pairs. U.S. Pat. No. 6,673,610 and U.S. published application 2002/0083488 require using fragments produced by digesting of the parent DNA strand as a megaprimer for obtaining a circular DNA used in transformation. U.S. Pat. No. 6,335,160 is directed to the gene assembly from overlapping fragments and generating a recombinant library. Finally, U.S. Pat. No. 5,354,670 requires two transformation steps and an intermediate treatment with a restriction.

Each of U.S. Pat. Nos. 7,176,004; 6,713,285; 6,391,548; and 5,932,419; and U.S. published applications 20040253729 and 20030032037 require two primers to anneal to two different strands for initiating amplification in opposite directions (i.e., forward and reverse primers) and to have complementary regions. U.S. Pat. Nos. 7,078,389 and 5,935,830 require a primer to comprise a mutagen (e.g., psoralen) that interacts with a template so that a triple-stranded molecule is formed.

U.S. published application 2006/0228786 require conducting polymerization of two strands using two different primers in two different reaction followed by annealing of the synthesized ssDNA molecules. U.S. published application 2003/0077613 are directed to a method for gene assembly and creating a library, wherein an assembled gene (ssDNA) is annealed with a scaffold DNA to fill gaps and generated dsDNA which is subcloned into a vector.

U.S published application 2004/0002057 describes a method for detecting a ligand in a sample which does not comprise mutagenesis. U.S. published application 2004/0002057 describes a method of establishing a mutant *E. coli* strain by using a mutagen in cultured cells. U.S. published application 2006/0199222 describes a generic method of directed evolution wherein mutated DNA is transformed into a particular, *Bacillus* strain.

There still exists a need for better and more effective method of generating a specific gene variants and a combinatorial gene library efficiently and quickly.

SUMMARY OF THE INVENTION

Unless specifically defined, all technical and scientific terms used herein have the meaning that would be commonly understood when viewed in context by a skilled artisan in the art providing the context, for example, chemistry, biochemistry, cellular biology, molecular biology, or medical sciences.

Accordingly, one object of the present invention is to provide a method of producing a plurality of modified polynucleotides having different combinations of various mutations at multiple sites by a tailored multi-site combinatorial assembly. The present invention allows making specific changes to a gene and reassembling mutations or changes at multiple sites of the gene. These and other objects of the present invention, which will become more apparent in conjunction with the following detailed description of the preferred embodiments, either alone or in combinations thereof, have been satisfied by the discovery of a method comprising:

(a) adding at least three primers to a double stranded template polynucleotide in a single reaction mixture, wherein the at least three primers are not overlapping, and wherein each of the at least three primers comprise at least one mutation different from the other primers, wherein at least one primer is a forward primer that can anneal to a minus strand of the template and at least one primer is a reverse primer that can anneal to a plus strand of the template, and (b) subjecting the reaction mixture to a polymerase extension reaction to yield a plurality of extended modified polynucleotides from the at least three primers.

In another embodiment, a method of producing a plurality of modified polynucleotides comprising the mutations of interest, comprises:

(a) adding at least two primers to a double stranded template polynucleotide in a single reaction mixture, wherein the at least two primers are not overlapping, and wherein each of the at least two primers comprise at least one mutation different from the other primer(s), wherein at least one primer is a forward primer that can anneal to a minus strand of the template and at least one primer is a reverse primer that can anneal to a plus strand of the template, (b) subjecting the reaction mixture to a polymerase extension reaction to yield a plurality of extended modified polynucleotides from the at least two primers, (c) treating the plurality of extended modified polynucleotides with an enzyme, thereby destroying the template polynucleotide, (d) transforming the treated extended modified polynucleotides that have not been treated with a ligase into a cell, (e) recovering the plurality of extended modified polynucleotides from the cell, and (f) selecting the plurality of extended modified polynucleotides comprising the mutations of interest.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless expressly stated otherwise, the techniques employed or contemplated herein are standard methodologies well known to one of ordinary skill in the art. The examples of embodiments are for illustration purposes only.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 5. A map of primers annealing in a six mutation assembly.

FIG. 11. A map of primers annealing in a three mutation assembly.

DETAILED DESCRIPTION OF THE PREFERRED EMBODIMENTS

The TMCA method can generate a specific gene variant comprising multiple changes or a combinatorial gene library efficiently and quickly; requires minimum cost and effort; and can be tailored to make biased combinatorial library according to the "needs." The TMCA method can be performed without employing a ligation step and, therefore, simplifies the process of generating multiple mutations. The "needs" of a particular library vary by experiments. Potential mutation sites—the "needs"—for example, may be either 1) rationally designed amino acid changes or 2) individual amino acids alterations empirically determined to produce a desired effect on an enzyme (determined by GSSM$^{SM}$ and screening efforts). Each library is created with a specific number of potential mutation sites. It may be preferable to create a library biased towards progeny with either more or less mutations at the potential mutation sites. Likewise, it may be preferable to create a library in which a bias exists towards or against a particular mutation or mutation site.

All methods and materials similar or equivalent to those described herein can be used in the practice or testing of the present invention, with suitable methods and materials being described herein. All publications, patent applications, patents, and other references mentioned herein are incorporated by reference in their entirety. Further, the materials, methods, and examples are illustrative only and are not intended to be limiting, unless otherwise specified.

Figure 1:
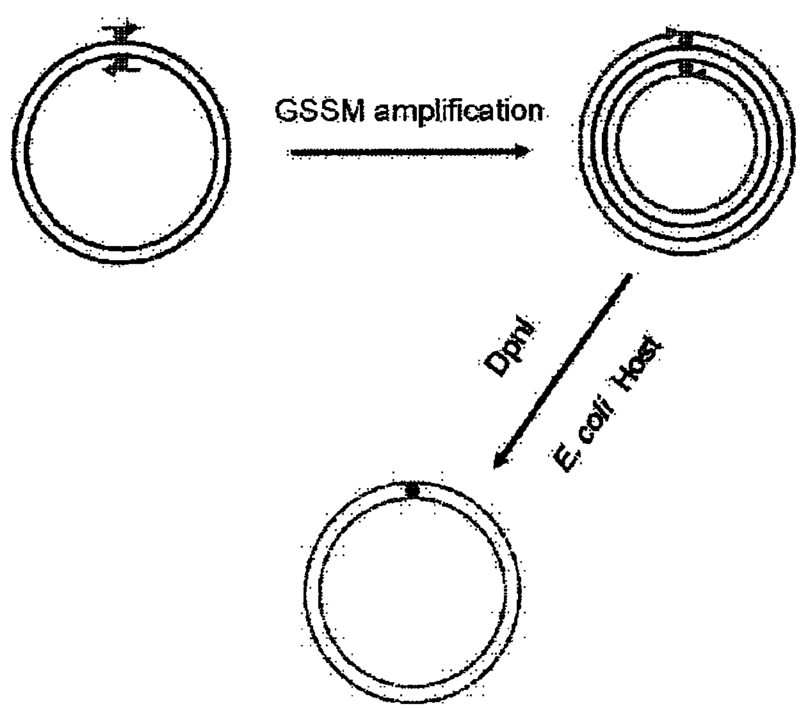
FIG. 1. A schematic representation of GSSM$^{SM}$.
Figure 2:
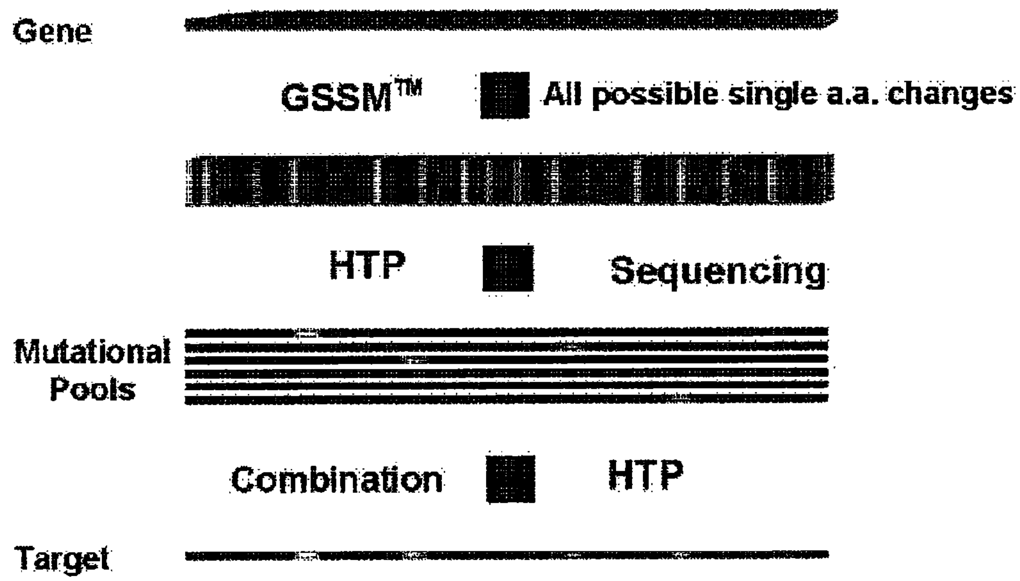
FIG. 2. A schematic representation of an evolution-GSSM$^{SM}$ process flow.
Figure 3:
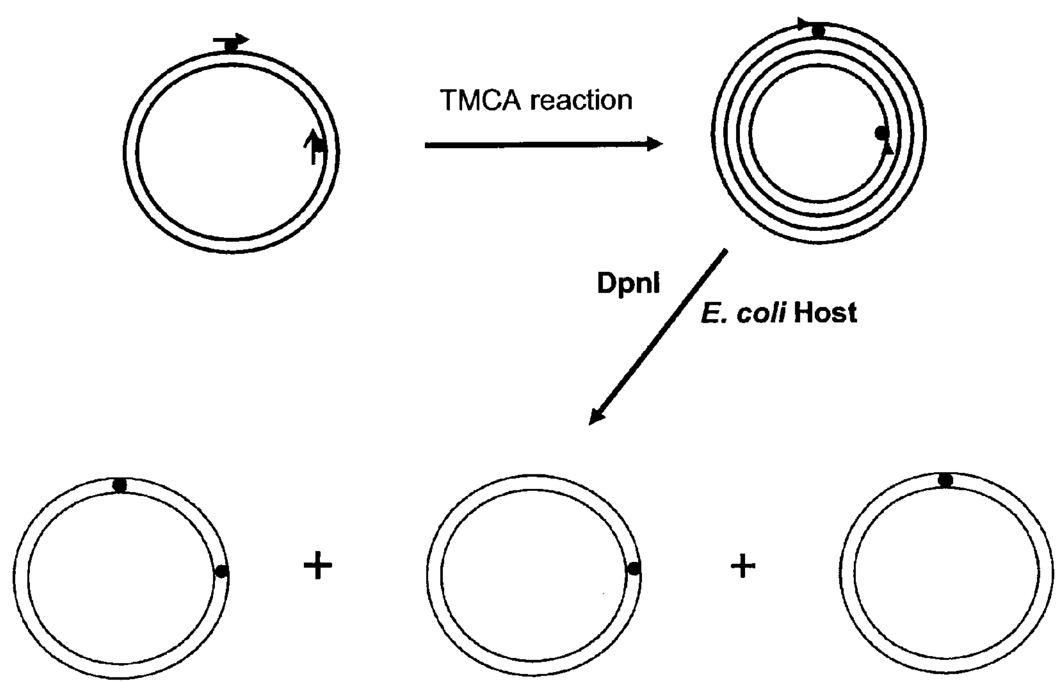
FIG. 3. A schematic representation of a tailored multi-site combinatorial assembly.

In this application, the present inventors designed a method of a tailored multi-site combinatorial assembly illustrated generally in FIG. 3. For comparison, FIG. 1 and FIG. 2 illustrate evolution-Gene Site Saturated Mutagenesis ("GSSM") in which each mutation position may contain two or more mutations for different amino acids. The evolution-GSSM$^{SM}$ can be used for introducing nucleotide changes into a specific gene and to mutate each codon of an open reading frame to all other amino acids for one residue or more at a time. Thus, a GSSM$^{SM}$ library is created, wherein a single clone comprises DNA having one change, while the progeny polypeptides in a library created by the TMCA method may comprise multiple mutations, preferably, two or more, more preferably three or more, more preferably four or more, five or more, six or more, eight or more, ten or more, and more preferably twelve or more mutations.

Using the GSSM$^{SM}$ technique, one residue is changed at a time to cover all 20 amino acids. The library is screened and up-mutants identified. The TMCA reaction is designed for making mutations at multiple sites of one molecule. The TMCA reaction can be used to combine the up-mutants identified from the GSSM$^{SM}$ library. Under the conditions of the TMCA reaction, one would expect formation of multiple PCR products. The PCR products are not expected to be transformed into the cells and to be amplified.

Within the context of the present invention, the term "amino acid," as used herein refers to any organic compound that contains an amino group (—$NH_2$) and a carboxyl group (—COOH); preferably either as free groups or alternatively after condensation as part of peptide bonds. The "twenty naturally occurring amino acids" are understood in the art and refer to: alanine (ala or A), arginine (arg or R), asparagine (asn or N), aspartic acid (asp or D), cysteine (cys or C), gluatamic acid (glu or E), glutamine (gln or Q), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (trp or W), tyrosine (tyr or Y), and valine (val or V).

The term "amplification" ("a polymerase extension reaction") means that the number of copies of a polynucleotide is increased.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference "TATAC" and is complementary to a reference sequence "GTATA."

A "primer" is defined herein as a nucleic acid strand that can anneal to a template nucleic acid and serves as a starting point for DNA amplification. The primer can be entirely or partially complementary to a specific region of the template polynucleotide. A non-complementary nucleotide is defined herein as a mismatch. A mismatch may be located within the primer or at the either end of the primer. Preferably, a single nucleotide mismatch, more preferably two, and more preferably, three or more consecutive or not consecutive nucleotide mismatches is (are) located within the primer. The primer has from 6 to 200 nucleotides, preferably, from 20 to 80 nucleotides, and more preferably, from 43 to 65 nucleotides. More preferably, the primer has 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, or 190 nucleotides. A "forward primer" as defined herein is a primer that is complementary to a minus strand of the template polynucleotide. A "reverse primer" as defined herein is a primer complementary to a plus strand of the template polynucleotide. Preferably, the forward and reverse primers do not comprise overlapping nucleotide sequences. "Do not comprise overlapping nucleotide sequences" as defined herein means that a forward and reverse primer does not anneal to a region of the minus and plus strands, respectively, of the template polynucleotide in which the plus and minus strands are complimentary to one another. With regard to the primers annealing to the same strand of the template polynucleotide, "do not comprise overlapping nucleotide sequences" means the primers do not comprise sequences complementary to the same region of the same strand of the template polynucleotide.

The plus strand is the same as the sense strand and can also be called the coding or non-template strand. This is the strand that has the same sequence as the mRNA (except it has Ts instead of Us). The other strand, called the template, minus, or antisense strand, is complementary to the mRNA.

Figure 4:
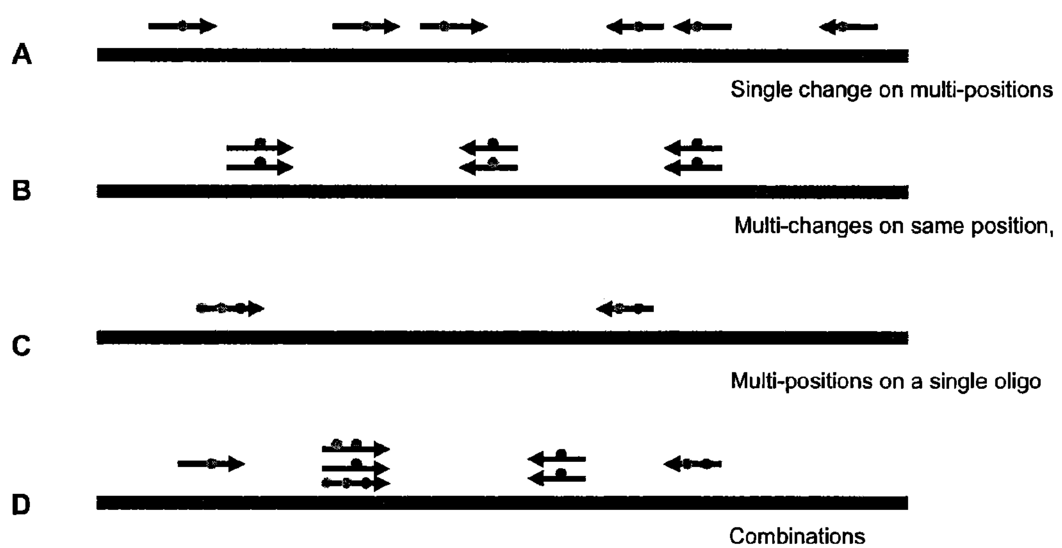
FIG. 4 A-D. Combinations of primers in the TMCA reaction.

"Primers covering the same selected region of the template polynucleotide" is defined herein as a set of degenerate primers each comprising at least one degenerate position, wherein the mutation of interest is a range of different nucleotides at the degenerate position, or a set of degenerate primers comprising at least one degenerate codon corresponding to at least one codon of the template polynucleotide, or a combination thereof For example, a set of primers for all possible combinations for three codon mutations Y276F/S282L, H, P, R, or C/L284F (see e.g., FIG. 4, 15, or 16) are the primers covering the same region of the template. "Primers covering the same selected region of the template polynucleotide" can also be, for example, a combination of specific primers.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction may be electrophoresed on a gel.

"Recombinant" enzymes refer to enzymes produced by recombinant DNA techniques, i.e., produced from cells transformed by an exogenous DNA construct encoding the desired enzyme. "Synthetic" enzymes are those prepared by chemical synthesis.

The term "restriction site" refers to a recognition sequence that is necessary for the manifestation of the action of a restriction enzyme, and includes a site of catalytic cleavage. It is appreciated that a site of cleavage may or may not be contained within a portion of a restriction site that comprises a low ambiguity sequence (i.e. a sequence containing the principal determinant of the frequency of occurrence of the restriction site). Thus, in many cases, relevant restriction sites contain only a low ambiguity sequence with an internal cleavage site (e.g. G/AATTC in the EcoRI site) or an immediately adjacent cleavage site (e.g. /CCWGG in the EcoRII site). In other cases, relevant restriction enzymes (e.g. the Eco57I site or CTGAAG(16/14)) contain a low ambiguity sequence (e.g. the CTGAAG sequence in the Eco57I site) with an external cleavage site (e.g. in the $N_{16}$ portion of the Eco57I site). When an enzyme (e.g. a restriction enzyme) is said to "cleave" a polynucleotide, it is understood to mean that the restriction enzyme catalyzes or facilitates a cleavage of a polynucleotide.

An "ambiguous base requirement" in a restriction site refers to a nucleotide base requirement that is not specified to the fullest extent, i.e. that is not a specific base (such as, in a non-limiting exemplification, a specific base selected from A, C, G and T), but rather may be any one of at least two or more bases. Commonly accepted abbreviations that are used in the art as well as herein to represent ambiguity in bases include the following: R=G or A; Y=C or T; M=A or C; K=G or T; S=G or C; W=A or T; H=A or C or T; B=G or T or C; V=G or C or A; D=G or A or T; N=A or C or G or T.

A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith (Smith and Waterman, Adv Appl Math, 1981; Smith and Waterman, J Teor Biol, 1981; Smith and Waterman, J Mol Biol, 1981; Smith et al, J Mol Evol, 1981), by the homology alignment algorithm of Needleman (Needleman and Wuncsch, 1970), by the search of similarity method of Pearson (Pearson and Lipman, 1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

"Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The terms "fragment", "derivative" and "analog" when referring to a reference polypeptide comprise a polypeptide which retains at least one biological function or activity that is at least essentially same as that of the reference polypeptide. Furthermore, the terms "fragment", "derivative" or "analog" are exemplified by a "pro-form" molecule, such as a low activity proprotein that can be modified by cleavage to produce a mature enzyme with significantly higher activity.

The term "gene" means the segment of DNA involved in producing a polypeptide chain; it includes regions preceding and following the coding region (leader and trailer) as well as intervening sequences (introns) between individual coding segments (exons).

The term "heterologous" means that one single-stranded nucleic acid sequence is unable to hybridize to another single-stranded nucleic acid sequence or its complement. Thus areas of heterology mean that areas of polynucleotides or polynucleotides have areas or regions within their sequence which are unable to hybridize to another nucleic acid or polynucleotide. Such regions or areas are for example areas of mutations.

The term "homologous" or "homeologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentrations as discussed later. Preferably the region of identity is greater than about 5 bp, more preferably the region of identity is greater than 10 bp.

The term "identical" or "identity" means that two nucleic acid sequences have the same sequence or a complementary sequence. Thus, "areas of identity" means that regions or areas of a polynucleotide or the overall polynucleotide are identical or complementary to areas of another polynucleotide or the polynucleotide.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

By "isolated nucleic acid" is meant a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

"Ligation" refers to the process of forming phosphodiester bonds between nucleic acid strands (Sambrook et al, 1982, p. 146; Sambrook, 1989). DNA ligase can link together two DNA strands that have single-strand breaks (a break in both complementary strands of DNA). The alternative, a double-strand break, is fixed by a different type of DNA ligase using the complementary strand as a template but still requires DNA ligase to create the final phosphodiester bond to fully repair the DNA. Unless otherwise provided, ligation may be accomplished using known buffers and conditions with 10 units of T4 DNA ligase ("ligase") per 0.5 μg of approximately equimolar amounts of the DNA fragments to be ligated. "Products are not ligated" refers to not forming phosphodiester bonds between the ends of a nucleic acid obtained by amplifying the whole circular double-stranded template polynucleotide by using primers.

The term "mutations" is defined as changes in the sequence of a wild-type or parental nucleic acid sequence or changes in the sequence of a peptide. Such mutations may be point mutations such as transitions or transversions. A mutation may be a change to one or more nucleotides or encoded amino acid sequences. The mutations may be deletions, insertions or duplications.

As used herein, the degenerate "N,N,N" nucleotide sequence represents triplets, where "N" can be A, C, G or T.

The term "naturally-occurring" as used herein as applied to the object refers to the fact that an object can be found in nature. For example, a polypeptide or polynucleotide sequence that is present in an organism (including viruses) that can be isolated from a source in nature and which has not been intentionally modified by man in the laboratory is naturally occurring. Generally, the term naturally occurring refers to an object as present in a non-pathological (undiseased) individual, such as would be typical for the species.

As used herein, a "nucleic acid molecule" is comprised of at least one base or one base pair, depending on whether it is single-stranded or double-stranded, respectively. Furthermore, a nucleic acid molecule may belong exclusively or chimerically to any group of nucleotide-containing molecules, as exemplified by, but not limited to, the following groups of nucleic acid molecules: RNA, DNA, genomic nucleic acids, non-genomic nucleic acids, naturally occurring and not naturally occurring nucleic acids, and synthetic nucleic acids. This includes, by way of non-limiting example, nucleic acids associated with any organelle, such as the mitochondria, ribosomal RNA, and nucleic acid molecules comprised chimerically of one or more components that are not naturally occurring along with naturally occurring components. Additionally, a "nucleic acid molecule" may contain in part one or more non-nucleotide-based components as exemplified by, but not limited to, amino acids and sugars. Thus, by way of example, but not limitation, a ribozyme that is in part nucleotide-based and in part protein-based is considered a "nucleic acid molecule." In addition, by way of example, but not limitation, a nucleic acid molecule that is labeled with a detectable moiety, such as a radioactive or alternatively a non-radioactive label, is likewise considered a "nucleic acid molecule."

The terms "nucleic acid sequence coding for" or a "DNA coding sequence of" or a "nucleotide sequence encoding" a particular protein or polypeptide refer to a DNA sequence which is transcribed and translated into a protein or polypeptide when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

The terms "nucleic acid encoding a protein or peptide" or "DNA encoding a protein or peptide" or "polynucleotide encoding a protein or peptide" and other synonymous terms encompasses a polynucleotide which includes only coding sequence for the protein or peptide as well as a polynucleotide which includes additional coding and/or non-coding sequence.

Accordingly, in a non-limiting embodiment, a "nucleic acid library" is comprised of a vector-based collection of one or more nucleic acid molecules. In another preferred embodiment a "nucleic acid library" is comprised of a non-vector-based collection of nucleic acid molecules. In yet another preferred embodiment a "nucleic acid library" is comprised of a combined collection of nucleic acid molecules that is in part vector-based and in part non-vector-based. Preferably, the collection of molecules comprising a library is searchable and separable according to individual nucleic acid molecule species.

An "oligonucleotide" (or synonymously an "oligo") refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated.

As used herein the term "parental polynucleotide set" is a set comprised of one or more distinct polynucleotide species. Usually this term is used in reference to a progeny polynucleotide set which is preferably obtained by mutagenization of the parental set, in which case the terms "parental, "starting and "template" are used interchangeably.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50-200 mM NaCl or KCl, pH 6.5-8.5, 20-45° C. and 0.001-10 mM divalent cation (e.g., $Mg^{++}$, $Ca^{++}$); preferably about 150 mM NaCl or KCl, pH 7.2-7.6, 5 mM divalent cation, and often include 0.01-1.0 percent nonspecific protein (e.g., BSA). A non-ionic detergent (Tween, NP-40, Triton X-100) can often be present, usually at about 0.001 to 2%, typically 0.05-0.2% (v/v). Particular aqueous conditions may be selected by the practitioner according to conventional methods. For general guidance, the following buffered aqueous conditions may be applicable: 10-250 mM NaCl, 5-50 mM Tris-HCl, pH 5-8, with optional addition of divalent cation(s) and/or metal chelators and/or non-ionic detergents and/or membrane fractions and/or anti-foam agents and/or scintillants.

Standard convention (5' to 3') is used herein to describe the sequence of double-stranded polynucleotides.

The term "related polynucleotides" means that regions or areas of the polynucleotides are identical and regions or areas of the polynucleotides are heterologous.

"Specific hybridization" is defined herein as the formation of hybrids between a first polynucleotide and a second polynucleotide (e.g., a polynucleotide having a distinct but substantially identical sequence to the first polynucleotide), wherein substantially unrelated polynucleotide sequences do not form hybrids in the mixture.

"Stringent hybridization conditions" means hybridization will occur only if there is at least 90% identity, preferably at least 95% identity and most preferably at least 97% identity between the sequences. See Sambrook et al, 1989, which is hereby incorporated by reference in its entirety.

The term "wild-type" means that the polynucleotide does not comprise any mutations. A "wild type" protein means that the protein will be active at a level of activity found in nature and will comprise the amino acid sequence found in nature.

Sources of the original polynucleotides may be isolated from individual organisms ("isolates"), collections of organisms that have been grown in defined media ("enrichment cultures"), or, most preferably, uncultivated organisms ("environmental samples"). The use of a culture-independent approach to derive polynucleotides encoding novel bioactivities from environmental samples is most preferable since it allows one to access untapped resources of biodiversity.

The microorganisms from which the polynucleotide may be prepared include prokaryotic microorganisms, such as Eubacteria and Archaebacteria, and lower eukaryotic microorganisms such as fungi, some algae and protozoa. Polynucleotides may be isolated from environmental samples in which case the nucleic acid may be recovered without culturing of an organism or recovered from one or more cultured organisms. In one aspect, such microorganisms may be extremophiles, such as hyperthermophiles, psychrophiles, psychrotrophs, halophiles, barophiles and acidophiles.

Polynucleotides selected and isolated as hereinabove described are introduced into a suitable host cell. The selected polynucleotides are preferably already in a vector which includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (Davis et al, 1986).

As representative examples of appropriate hosts, there may be mentioned: bacterial cells, such as *E. coli* and *Pseudomonas fluorescens;* bacteriophage; fungal cells, such as yeast, *Pichia pastoris* and *Aspergillus niger;* insect cells such as *Drosophila* S2 and *Spodoptera* Sf9; animal cells such as CHO, COS or Bowes melanoma; adenoviruses; and plant cells. The TMCA library can be made in, for example, in *E. coli* cells in the plasmid form, then the library can be further introduced into other hosts. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described in "SV40-transformed simian cells support the replication of early SV40 mutants" (Gluzman 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan.

As representative examples of expression vectors which may be used there may be mentioned viral particles, baculovirus, phage, plasmids, phagemids, cosmids, fosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, aspergillus* and yeast). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript plasmids, pNH vectors, (lambda-ZAP vectors (Stratagene); ptrc99a, pKK(223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used as long as they are replicable and viable in the host. Low copy number or high copy number vectors may be employed with the present invention.

A preferred type of vector for use in the present invention contains an f-factor origin replication. The f-factor (or fertility factor) in *E. coli* is a plasmid which effects high frequency transfer of itself during conjugation and less frequent transfer of the bacterial chromosome itself. A particularly preferred embodiment is to use cloning vectors, referred to as "fosmids" or bacterial artificial chromosome (BAC) vectors. These are derived from *E. coli* f-factor which is able to stably integrate large segments of genomic DNA. When integrated with DNA from a mixed uncultured environmental sample, this makes it possible to achieve large genomic fragments in the form of a stable "environmental DNA library."

Another preferred type of vector for use in the present invention is a cosmid vector. Cosmid vectors were originally designed to clone and propagate large segments of genomic DNA. Cloning into cosmid vectors is described in detail in "Molecular Cloning: A laboratory Manual" (Sambrook et al, 1989).

The DNA sequence in the expression vector is operatively linked to an appropriate expression control sequence(s) (promoter) to direct RNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

Generally, recombinant expression vectors will include origins of replication and selectable markers permitting transformation of the host cell, e.g., the ampicillin resistance gene of *E. coli* and *S. cerevisiae* TRP 1 gene, and a promoter derived from a highly-expressed gene to direct transcription of a downstream structural sequence. Such promoters can be derived from operons encoding glycolytic enzymes such as 3-phosphoglycerate kinase (PGK), .alpha.-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium.

The cloning strategy permits expression via both vector driven and endogenous promoters; vector promotion may be important with expression of genes whose endogenous promoter will not function in *E. coli.*

The DNA isolated or derived from microorganisms can preferably be inserted into a vector or a plasmid prior to probing for selected DNA. Such vectors or plasmids are preferably those containing expression regulatory sequences, including promoters, enhancers and the like. Such polynucleotides can be part of a vector and/or a composition and still be isolated, in that such vector or composition is not part of its natural environment. Particularly preferred phage or plasmid and methods for introduction and packaging into them are described in detail in the protocol set forth herein.

Any source of nucleic acid, in purified form can be utilized as the starting nucleic acid (also defined as "a template polynucleotide"). Thus, the process may employ DNA or RNA including messenger RNA, which DNA or RNA can be single-stranded, and preferably double stranded. In addition, a DNA-RNA hybrid which contains one strand of each may be utilized. The nucleic acid sequence may be of various lengths depending on the size of the nucleic acid sequence to be mutated. Preferably the specific nucleic acid sequence is from 50 to 50000 base pairs, and more preferably from 50-11000 base pairs.

The nucleic acid may be obtained from any source, for example, from plasmids such a pBR322, from cloned DNA or RNA or from natural DNA or RNA from any source including bacteria, yeast, viruses and higher organisms such as plants or animals. DNA or RNA may be extracted from blood or tissue material. The template polynucleotide may be obtained by amplification using the polynucleotide chain reaction (PCR, see U.S. Pat. No. 4,683,202 and U.S. Pat. No. 4,683,195). Alternatively, the polynucleotide may be present in a vector present in a cell and sufficient nucleic acid may be obtained by culturing the cell and extracting the nucleic acid from the cell by methods known in the art.

The initial small population of the specific nucleic acid sequences having mutations may be created by a number of different methods. Mutations may be created by error-prone PCR. Error-prone PCR uses low-fidelity polymerization conditions to introduce a low level of point mutations randomly over a long sequence. Alternatively, mutations can be introduced into the template polynucleotide by oligonucleotide-directed mutagenesis. In oligonucleotide-directed mutagenesis, a short sequence of the polynucleotide is removed from the polynucleotide using restriction enzyme digestion and is replaced with a synthetic polynucleotide in which various bases have been altered from the original sequence. The polynucleotide sequence can also be altered by chemical mutagenesis. Chemical mutagens include, for example, sodium bisulfite, nitrous acid, hydroxylamine, hydrazine or formic acid. Other agents which are analogues of nucleotide precursors include nitrosoguanidine, 5-bromouracil, 2-aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X-rays or ultraviolet light. Generally, plasmid polynucleotides so mutagenized are introduced into *E. coli* and propagated as a pool or library of hybrid plasmids.

Alternatively the small mixed population of specific nucleic acids may be found in nature in that they may consist of different alleles of the same gene or the same gene from different related species (i.e., cognate genes). Alternatively, they may be related DNA sequences found within one species, for example, the immunoglobulin genes.

Once the mixed population of the specific nucleic acid sequences is generated, the polynucleotides can be used directly or inserted into an appropriate cloning vector, using techniques well-known in the art.

The choice of vector depends on the size of the polynucleotide sequence and the host cell to be employed in the methods of this invention. The templates of this invention may be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids are preferred where the specific nucleic acid sequence to be mutated is larger because these vectors are able to stably propagate large polynucleotides.

For simplicity, the TMCA method of the invention will be explained with intent to assemble six point mutations at six different sites.

Figure 5:
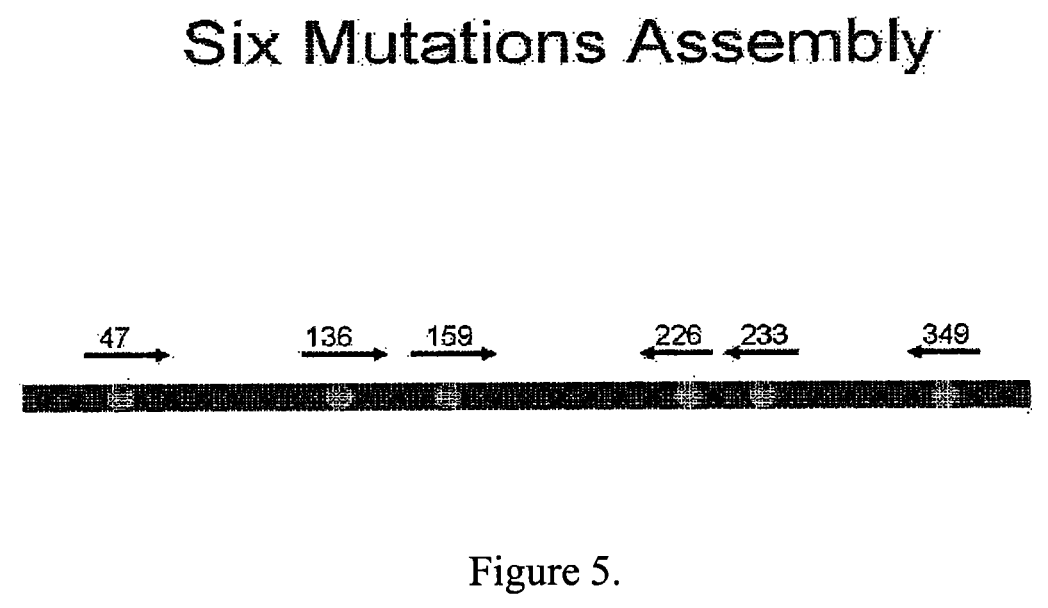

First, six primers are designed and synthesized. Each primer contains a point mutation compared to the wild type sequence. Three oligos are designed as forward primers and three are designed as reverse primers to anneal to the gene (FIG. 5). All six oligos are mixed together and used to set up TMCA reactions under the conditions detailed in the Examples. Then, the finished TMCA reactions are verified by agarose gels to determine if the reactions are successful. The Dpn1 restriction enzyme is added to the TMCA reactions to destroy the template circular DNA. In order for the Dpn1 to work, the template DNA has to be from an *E. coli* host which can methylate the DNA. The Dpn1-treated reactions are transformed into *E. coli* cells to recover the DNAs with desired mutations. The transformants are screened by sequencing or desired assay.

The method of the invention is not limited to six sites. Higher or lower number of positions can be assembled by this method. It is also not limited to a single change at one position. Multiple primers can be designed to cover different changes at the same position, with single change on each primer. *E. coli* has been used for the demonstration; however, other bacterial hosts would work for this method. The method of the invention can not only introduce point mutation, it can also make deletions or insertions or multiple mutations with degenerated primers.

The TMCA reactions can be altered with primer concentration, primer Tm (annealing temperature to a template), DNA polymerase, template concentration, combination of the primers and different host to control how the changes at different sites are assembled.

The assembly may occur in vitro or in vivo or a combination of both. FIG. 5 illustrates a map of the primers annealing to a gene. The main use of the method of the invention is for the combinatorial reassembly of GSSM$^{SM}$ up-mutants. However, the method of the invention can be also useful, for example, for any other applications listed below.

1. TMCA can be used to make specific changes to a gene, including mutation, deletion and insertion.

2. TMCA can be used to make a specific gene variant based on a wild type gene.

3. TMCA can be used to combine mutation, deletion or insertion.

4. TMCA can be used to make a combinatorial library of mutation, deletion or insertion in a controllable manner.

5. TMCA can be used to make a combinatorial multi-site GSSM$^{SM}$ library.

In general, the present invention provides a method for producing a plurality of progeny polynucleotides having different combinations of various mutations at multiple sites. The method can be performed in part by a combination of at least one or more of the following steps:

Obtaining sequence information of a polynucleotide ("first" or "template"). For example, the sequence can be a wild type, mutated wild type, or non-naturally occurring sequence. The sequence information can be of the complete polynucleotide or of partial regions of interest, such as a sequence encoding a site for binding, binding-specificity, catalysis, or substrate-specificity. The polynucleotide can comprise a sequence such as an open reading frame, a gene, a polypeptide-encoding sequence, or an enzyme-encoding sequence, with or without a signal or secretion sequence.

Identifying three or more mutations of interest along the sequence of the polynucleotide, such as mutations at 3, 4, 5, 6, 8, 10, 12, 20 or more positions. The mutations can be at the polynucleotide sequence level or mutations to the amino acid sequence encoded by the polynucleotide sequence, e.g., codons. The positions can be predetermined by absolute position or by the context of surrounding residues or homology. The sequences flanking the mutation positions on either side are preferably known. Each mutation position may contain two or more mutations, such as for different amino acids. Such mutations can be identified by using Gene Site Saturation Mutagenesis (GSSM), as described above, and in U.S. Pat. No. 6,171,820, No. 6,562,594, or No. 6,764,835.

Providing primers comprising the mutations of interest relative to the template sequence. The primers can be synthetic oligonucleotides. Preferably, a primer is provided for each mutation of interest. The mutations can be changes in one or more nucleotide or encoded amino acid sequences, insertions or deletions. Thus, a position having 3 mutations of interest can use 3 primers at that position. The primer can also be provided as a pool of primers containing a degenerate position so that the mutation of interest is the range of any nucleotide or naturally occurring amino acid, or a subset of that range. For example, a pool of primers can be provided that favor mutations for aliphatic amino acid residues.

The primers can be prepared as forward or reverse primers, preferably at least one forward primer and at least one reverse primer, and more preferably a relatively balanced number of each (e.g., 3 forward and 4 reverse). The 3 forward primers can be selected for relatively adjacent, with similarly adjacent reverse primers, e.g., 1F, 2F, 3F, 4R, 5R, 6R, 7R. When mutations are positioned closely together, it can be convenient to use primers that contain mutations for more than one position or different combinations of mutations at multiple positions.

Providing a polynucleotide containing the template polynucleotide. The polynucleotide is preferably circular, more preferably super-coiled, such as a plasmid or vector for cloning, sequencing or expression. The polynucleotide may be single-stranded ("ssDNA"), and preferably double-stranded ("dsDNA"). For example, the TCMA method subjects the supercoiled ("Sc") dsDNA template to a heating step at 95° C. for 1 min, the template does not become ssDNA (see Levy, *NAR*, 28(12):e57(i-vii) (2000), shows that heating sc dsDNA to 95° C. for 5 min does not produce ssDNA molecules and is reversible if the molecules are cooled after heating (pages ii-iii, FIG. 2)).

Adding the primers to the template polynucleotide in a reaction mixture under conditions that allow the primers to anneal to the polynucleotide. Preferably, the primers are added to the polynucleotide in a single reaction mixture, but can be added in multiple reactions according to an experimental design.

Performing a polymerase extension of the primers, preferably allowing the extension to proceed completely around a circular template molecule. The extension products (as defined herein, "progeny" or "modified extended polynucleotide") may be amplified by conventional means.

The products may be analyzed for length, sequence, desired nucleic acid properties, or expressed as polynucleotides and/or polypeptides. Other analysis methods include in-situ hybridization, sequence screening or expression screening. The analysis can include one or more rounds of screening and selecting for a desired property.

The products can also be transformed into a cell or other expression system, such as a cell-free system. The cell-free system may contain enzymes related to DNA replication, repair, recombination, transcription, or for translation. Exemplary hosts include bacterial, yeast, plant and animal cells and cell lines, and include *E. coli, Pseudomonas fluorescens, Pichia pastoris* and *Aspergillus niger*. For example, XL1-Blue or Stbl2 strains of *E. coli* can be used as hosts. When using *E. coli* with Dpn1 (which can be used to remove undesired template after reaction), the template DNA may be from an *E. coli* host that can methylate the DNA. The cells can be used for expression of the progeny polynucleotides.

Polynucleotides or polypeptide expression products can be retrieved from the cells and analyzed for length, sequence, desired nucleic acid properties, or expressed as polypeptides. The analysis can include one or more rounds of screening and selecting for a desired property.

The method of the invention may be used with the same or different primers under different reaction conditions to promote products having different combinations or numbers of mutations, such as under conditions 1A, 7A and 13A illustrated in the Examples.

By performing the method described above, the invention also provides one or more polynucleotides produced by the method, which can be screened or selected for a desired property. One or more of the progeny polynucleotides can be expressed as polypeptides, and optionally screened or selected for a desired property. Thus, the invention provides polynucleotides and polypeptides produced by the method of the invention, as well as libraries of such polynucleotides and polypeptides. The invention further provides for screening the libraries by screening or selecting the library to obtain one or more polynucleotides or polypeptides.

In one aspect of the invention, a preferred method of producing a plurality of modified polynucleotides, comprises:

(a) adding at least three primers to a double stranded template polynucleotide in a single reaction mixture, wherein the at least three primers are not overlapping, and wherein each of the at least three primers comprise at least one mutation different from the other primers, wherein at least one primer is a forward primer that can anneal to a minus strand of the template and at least one primer is a reverse primer that can anneal to a plus strand of the template, and (b) subjecting the reaction mixture to a polymerase extension reaction to yield a plurality of extended modified polynucleotides from the at least three primers.

In another aspect of the invention, a cell is transformed with the plurality of extended products that have not been treated with a ligase. In another aspect of the invention, the plurality of extended modified polynucleotides is recovered from the cell. In another embodiment, the recovered plurality of extended modified polynucleotides is analyzed, for example, by expressing at least one of the plurality of extended modified polynucleotides and analyzing the polypeptide expressed therefrom. In another embodiment, the plurality of extended modified polynucleotides comprising the mutations of interest is selected.

In one embodiment, the template polynucleotide is a circular DNA, for example, a plasmid or vector DNA. In another embodiment, the circular DNA is a supercoiled DNA.

In another aspect, sequence information regarding the template polynucleotide can be obtained, and three or more mutations of interest along the template polynucleotide can be identified. In another embodiment, products obtained by the polymerase extension can be analyzed before transforming the plurality of extended modified products to a cell.

In another aspect of the invention, products obtained by the polymerase extension are treated with an enzyme, preferably a restriction enzyme, and more preferably DpnI restriction enzyme, thereby destroying the template polynucleotide sequence. The treated products are transformed into a cell, preferably, an *E. coli* cell.

In another embodiment at least two, preferably at least three, more preferably, at least four, at least five, at least six, at least seven, at least eight, at least nine, at least ten, at least eleven, at least twelve, or more primers can be used. In one embodiment, each primer comprises a single point mutation (FIG. 4A). In another embodiment, two forward or two reverse primers comprise a different change in the same position on the template polynucleotide (FIG. 4B). In another aspect of the invention, at least one primer comprises at least two changes in different positions on the template polynucleotide (FIG. 4C). In yet another embodiment, at least one primer comprises at least two changes in different positions and at least two forward or two reverse primers comprise a different change in the same position on the template polynucleotide (FIG. 4D).

In one embodiment, the forward primers are grouped into a forward group and the reverse primers are grouped into a reverse group, and the primers in the forward group and the primers in the reverse group, independent of one another, are normalized to be equal concentration in the corresponding group regardless of positions on the template polynucleotide, and wherein after the normalization an equal amount of the forward and reverse primers is added to the reaction. In this normalization method, a combination of some positions may be biased. The bias can be due to, for example, a relatively low primer concentration at one position containing a single primer compared to a position containing multiple primers. "Positional bias" refers to resulting polynucleotides which show a strong preference for the incorporation of primers at a single position relative to the other positions within its forward or reverse primer group. This results in a combination of modified polynucleotides which may have a high percentage of mutations within a single primer position but a low percentage of mutations at another position within its forward or reverse primer group. This bias is unfavorable when the goal of the TMCA is to generate progeny polynucleotides comprising all possible combinations of changes to the template. The bias can be corrected, for example, by normalizing the primers as a pool at each position to be equal. Performing two rounds of the TMCA method can increase the yield of desired progeny polynucleotides comprising multiple changes to the template, wherein round II uses some of the variants obtained from round I.

In another embodiment, the primer normalization is performed by organizing the primers into multiple groups depending on their location on the template polynucleotide, wherein the primers covering the same selected region on the template are in one group; normalizing the grouped primers within each group to be equal concentration; pooling the forward primers within one group into a forward group and normalizing concentration between each group of the forward primers to be equal; pooling the reverse primers within one group into a reverse group and normalizing concentration between each group of the reverse primers to be equal; and adding an equal amount of the pooled forward and reversed primers into the reaction. No bias has been observed for position combinations.

In one embodiment, a set of degenerate primers each comprising a degenerate position is provided, wherein the mutation of interest is a range of different nucleotides at the degenerate position. In another embodiment, a set of degenerate primers is provided comprising at least one degenerate codon corresponding to at least one codon of the template polynucleotide and at least one adjacent sequence that is homologous to a sequence adjacent to the codon of the template polynucleotide sequence. In another embodiment, the degenerated codon is N,N,N and encodes any of 20 naturally occurring amino acids. In another embodiment, the degenerated codon encodes less than 20 naturally occurring amino acids.

In a different embodiment, a preferred method of producing a plurality of modified polynucleotides comprising the mutations of interest, comprises:

(a) adding at least two primers to a double stranded template polynucleotide in a single reaction mixture, wherein the at least two primers are not overlapping, and wherein each of the at least two primers comprise at least one mutation different from the other primer(s), wherein at least one primer is a forward primer that can anneal to a minus strand of the template and at least one primer is a reverse primer that can anneal to a plus strand of the template,
(b) subjecting the reaction mixture to a polymerase extension reaction to yield a plurality of extended modified polynucleotides from the at least two primers,
(c) treating the plurality of extended modified polynucleotides with an enzyme, thereby destroying the template polynucleotide,
(d) transforming the treated extended modified polynucleotides that have not been treated with a ligase into a cell,
(e) recovering the plurality of extended modified polynucleotides from the cell, and
(f) selecting the plurality of extended modified polynucleotides comprising the mutations of interest.

The following Examples show that single mutations at multiple sites of a template or gene can be combined successfully in a simple single reaction mixture, which is unexpected based on the know methods of generation mutations. The distribution of all possible combinations from the experiment closely images the distribution pattern from statistic calculation. The reactions can be tailored to create biased combinations based on need.

Under the GSSM$^{SM}$ technology, the TMCA technique does not employ complementary primers annealing to both positive and negative strands of the template polynucleotide. The reasonable expectation from the thermal cycling extension containing primers as described for this TMCA invention (forward and reverse groups in a single thermal cycle reaction) would be an exclusive collection of amplified linear polynucleotides defined by individual pairs of the forward and reverse primers. The TMCA condition set up is almost identical to the standard PCR conditions. One would have expected to produce multiple PCR products in the TMCA reaction, wherein each product has fewer than the full set of mutations encompassed by a set of primers used in a single reaction, for example, less than 6 mutations when 6 primers are used and each primer comprises 1 mutation. Further, the PCR products are not expected to be transformed into the cells and to be amplified. Surprisingly, the TMCA method can generate a specific gene variant comprising multiple changes in one molecule and can be performed without employing a ligation step, and, therefore, simplifies the process of generating multiple mutations.

EXAMPLES

Example 1

Exemplary Protocol of the TMCA procedure is shown below:

TMCA Reactions
↓
Dpnl Treatment
↓
Transformation into host
↓
Screen

1. Set up TMCA reactions

| Condition 1 | |
|---|---|
| Pfu 10x buffer | 2.5 μl |
| DMSO | 2.5 μl |
| dNTPs(10 mM) | 0.5 μl |
| Template DNA (25 ng/μl) | 1 μl |
| PfuTurbo | 0.5 μl |
| Water | 14 μl |
| Forward primer (5 μM) | 2 μl |
| Reverse primer (5 μM) | 2 μl |
| Total | 25 μl |

| Condition 2 | |
|---|---|
| Pfx Accu Buffer | 5 μl |
| Template DNA (25 ng/μl) | 1 μl |
| Pfx Accuprime | 0.4 μl |
| Water | 37.6 μl |
| Forward primer (5 μM) | 3 μl |
| Reverse primer (5 μM) | 3 μl |
| Total | 50 μl |

| Condition 3 | |
|---|---|
| Pfx Accu Buffer | 2.5 μl |
| Template DNA (25 ng/μl) | 1 μl |
| Pfx Accuprime | 0.2 μl |
| Water | 17.3 μl |
| Forward primer (5 μM) | 2 μl |
| Reverse primer (5 μM) | 2 μl |
| Total | 25 μl |

| Cycling | Robocycler | Perkin-Elmer | |
|---|---|---|---|
| Initial denaturation | 95° C.; 1 min | 95° C.; 3 min | |
| Denaturation | 95° C.; 45 sec | 95° C.; 45 sec | 20 cycles |
| Anneal | 50° C.; 1 min | 50° C.; 45 sec | 20 cycles |
| Extend | 68° C.; 2 min/kb | 68° C.; 2 min/kb | 20 cycles |
| Polish | 68° C.; 5 min | 68° C.; 5 min | |
| | 4° C.; Indefinitely | 4° C.; Indefinitely | |

2. Run 50 of TMCA reactions on agarose gel to determine if the reactions are successful.
3. Dilute 10 of Dpnl restriction enzyme in 3 μl of water and 1 μl of buffer 4 (New England Biolab). Add 5 μl diluted enzyme to each TMCA reaction. Incubate at 37 degree for 4-8 hours.
4. Transform the Dpnl-treated reactions to *E. coil* cells by standard transformation protocol.
5. The resulting colonies were screened by sequencing or desired assay.

Example 2

In the first experiment, six sites on a gene were chosen to be combined (FIG. 5). The reactions were set up using forward primers on three sites and three reverse primers on the remaining three sites. The variants from the reactions were identified by sequencing. There were sixty-four different possible combinations. Under condition 1, more variants with lower numbers of mutation sites were preferred (FIG.

Figure 6:
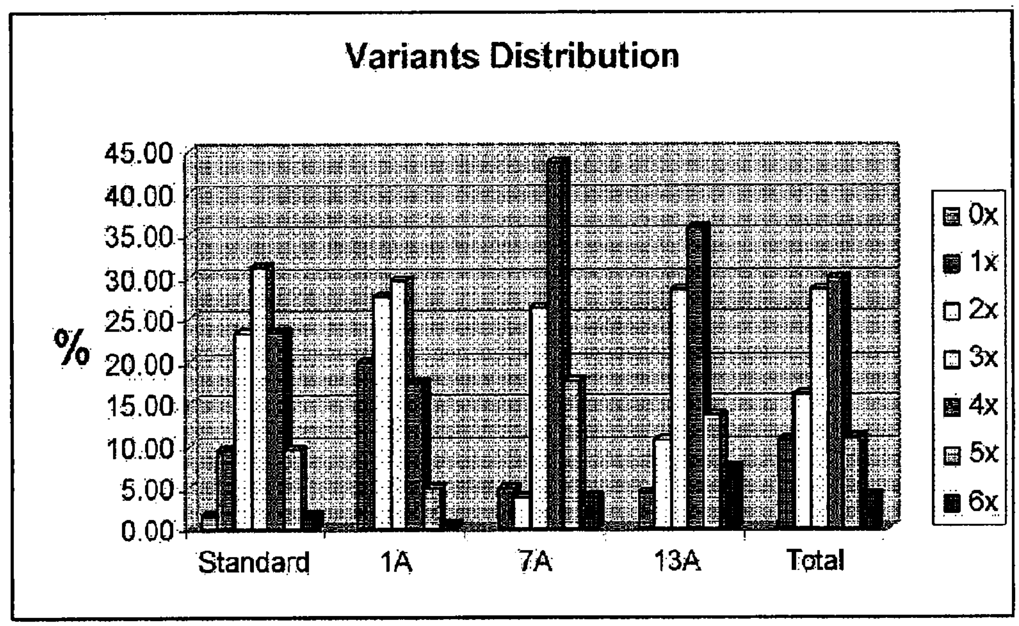
FIG. 6. Distribution of possible combinations with six mutation sites. Standard: calculated variant distribution under ideal situation; 1A: reaction condition 1 with *E. coli* strain XL1-Blue; 7A: reaction condition 2 with *E. coli* strain XL1-Blue; 13A: reaction condition 3 with *E. coli* strain XL1-Blue; Total: data combined from 1A, 7A and 13A; Ox: no mutation; 1×: single mutation; 2×: two mutations; 3×: three mutations; 4×: four mutations; 5×: five mutations; 6×: six mutations.
Figure 7:
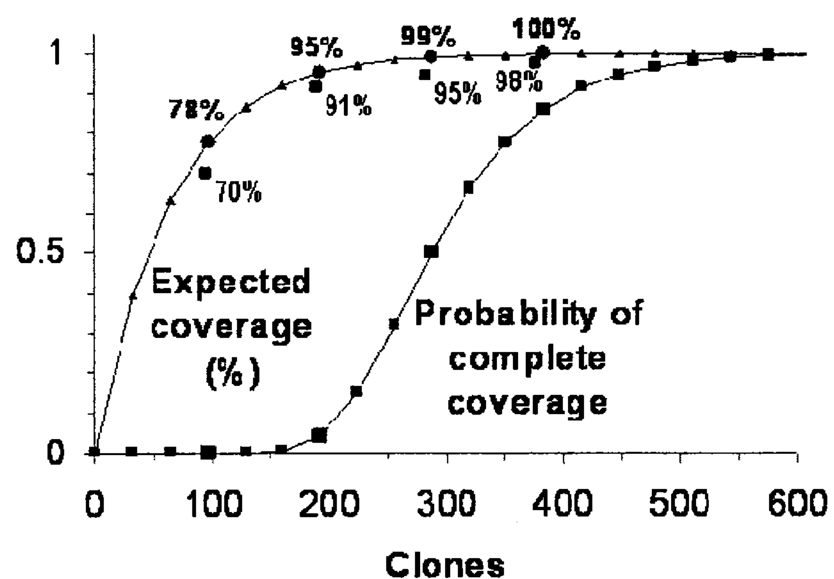
FIG. 7. Statistical calculations vs. experimental data in the six mutation assembly.

6). Under conditions 2 and 3, more variants with higher numbers of mutation sites were preferred (FIG. 6). The distribution of all possible combinations from the combined data (Total) was similar to the distribution pattern from statistic calculation (FIG. 6). One curve in FIG. 7 shows the expected coverage (%) of variants and another curve shows the probability of complete coverage when zero to six hundred clones are screened. The circles on the expected coverage (%) curve (i.e., 78%, 95%, 99%, and 100%) show expected coverage when 96, 192, 288 or 384 clones are screened. The squares below the expected coverage (%) curve (i.e., 70%, 91%, 95% and 98%) show the real coverage from the experimental data. The data shows an almost perfect match of expected coverage vs. real coverage.

TABLE 1

| Six Mutations Assembly | | | |
|---|---|---|---|
| Conditions | Screen | Unique Clones | Unique Clones |
| 1A | 1.5x | 69% (44/64) | 69% (44/64) |
| 1A | 3x | 80% (51/64) | 80% (51/64) |
| 7A | 1.5x | 63% (40/64) | 75% (42/64) |
| 13A | 1.5x | 61% (39/64) | 67% (43/64) |
| 13A | 3x | 76% (49/64) | 80% (51/64) |
| 1A + 7A | 3x | 91% (58/64) | 91% (58/64) |
| 1A + 7A | 4.5x | 94% (60/64) | 94% (60/64) |
| 1A + 13A | 3x | 91% (58/64) | 91% (58/64) |
| 1A + 13A | 4.5x | 95% (61/64) | 95% (61/64) |
| 1A + 13A | 6x | 98% (63/64) | 98% (63/64) |

Example 3

Figure 8:
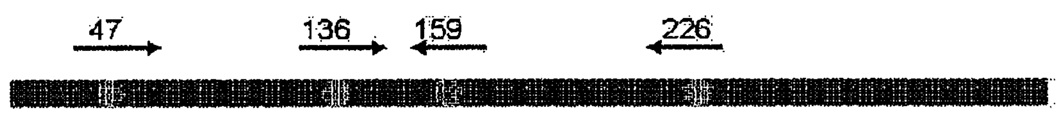
FIG. 8. A map of primers annealing in a four mutation assembly.
Figure 9:
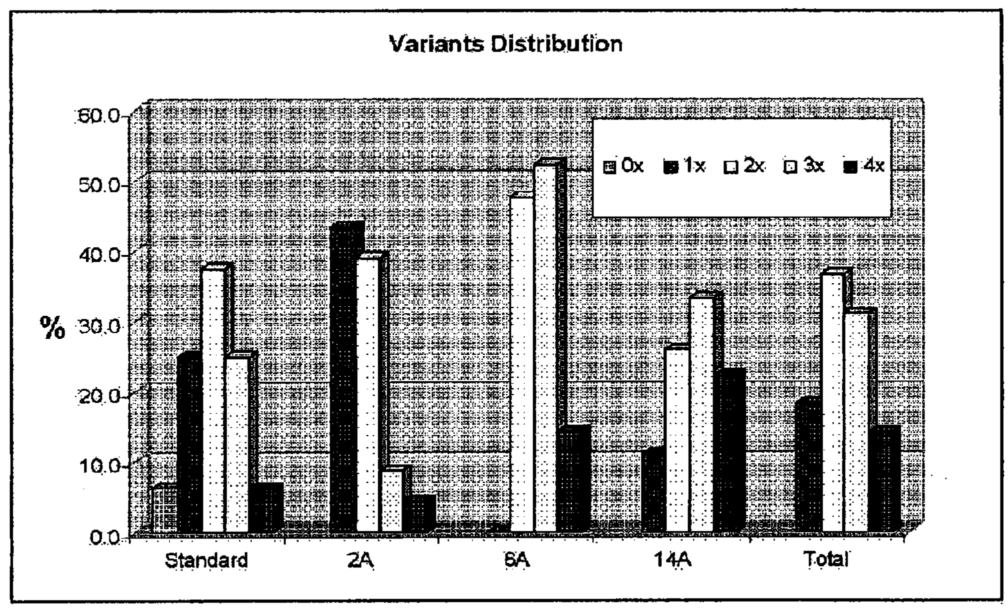
FIG. 9. Distribution of possible combinations with four mutation sites. Standard: calculated variant distribution under ideal situation; 2A: reaction condition 1 with *E. coli* strain XL1-Blue; 8A: reaction condition 2 with *E. coli* strain XL1-Blue; 14A: reaction condition 3 with *E. coli* strain XL1-Blue; Total: data combined from 2A, 8A and 14A; Ox: no mutation; 1×: single mutation; 2×: two mutations; 3×: three mutations; 4×: four mutations.
Figure 10:
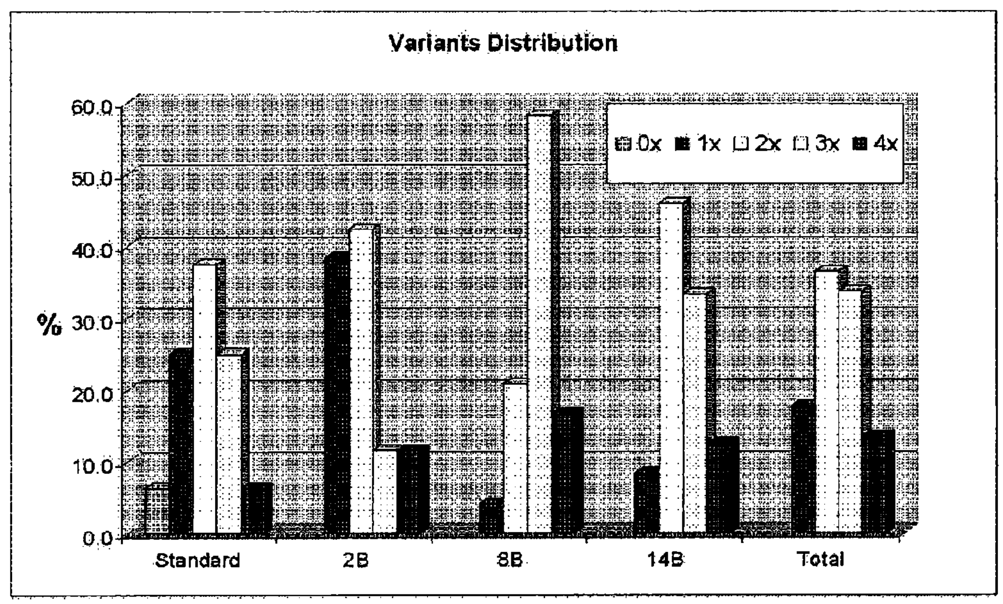
FIG. 10. Distribution of possible combinations with four sites. Standard: calculated variant distribution under ideal situation; 2B: reaction condition 1 with *E. coli* strain Stbl2; 8B: reaction condition 2 with *E. coli* strain Stbl2; 14B: reaction condition 3 with *E. coli* strain Stbl2; Total: data combined from 2B, 8B and 14B; Ox: no mutation; 1×: single mutation; 2×: two mutations; 3×: three mutations; 4×: four mutations.

In the second experiment, four sites on a gene were chosen to be combined (FIG. 8). The reactions were set up using forward primers on two sites and two reverse primers on the remaining two sites. The variants from the reactions were identified by sequencing. There were sixteen different possible combinations. Similar to the first experiment, condition 1 generated more variants with lower numbers of mutation sites and conditions 2 and 3 generated more variants with higher numbers of mutation sites (FIGS. 9 and 10). The distribution of all possible combinations from the combined data (Total) was similar to the distribution pattern from statistic calculation (FIGS. 9 and 10).

TABLE 2

| Four Mutations Assembly | | | |
|---|---|---|---|
| Conditions | Screen | Unique Clones | Unique Clones |
| 2A | 2x | 75% (12/16) | 81% (13/16) |
| 8A | 2x | 62% (10/16) | 87% (14/16) |
| 14A | 2x | 68% (11/16) | 75% (12/16) |
| 2A + 8A | 4x | 93% (15/16) | 100% (16/16) |
| 2A + 14A | 4x | 93% (15/16) | 93% (15/16) |
| 2B | 2x | 75% (12/16) | 75% (12/16) |
| 8B | 2x | 50% (8/16) | 68% (11/16) |
| 14B | 2x | 75% (12/16) | 87% (14/16) |
| 2B + 8B | 4x | 81% (13/16) | 81% (13/16) |
| 2B + 14B | 4x | 87% (14/16) | 87% (14/16) |

Example 4

Figure 11:
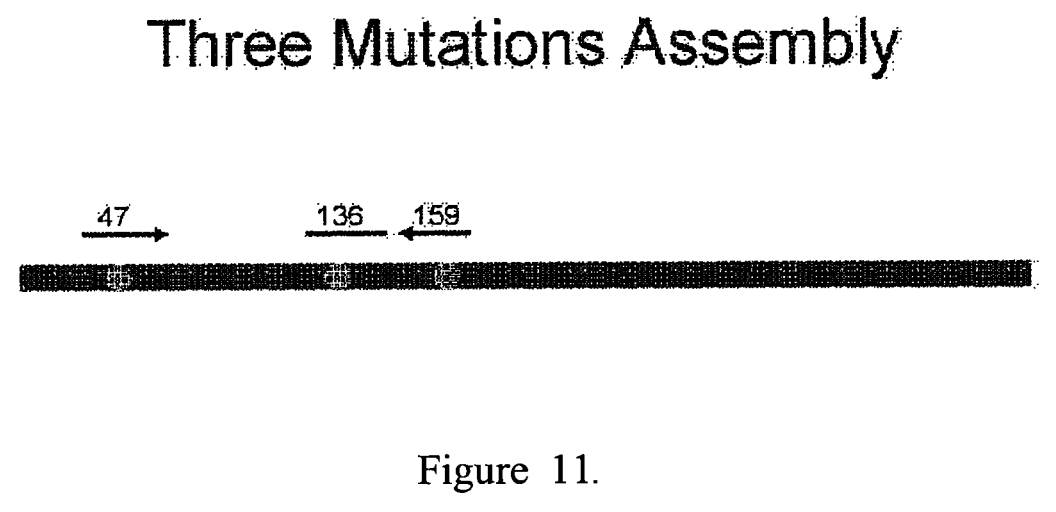
Figure 12:
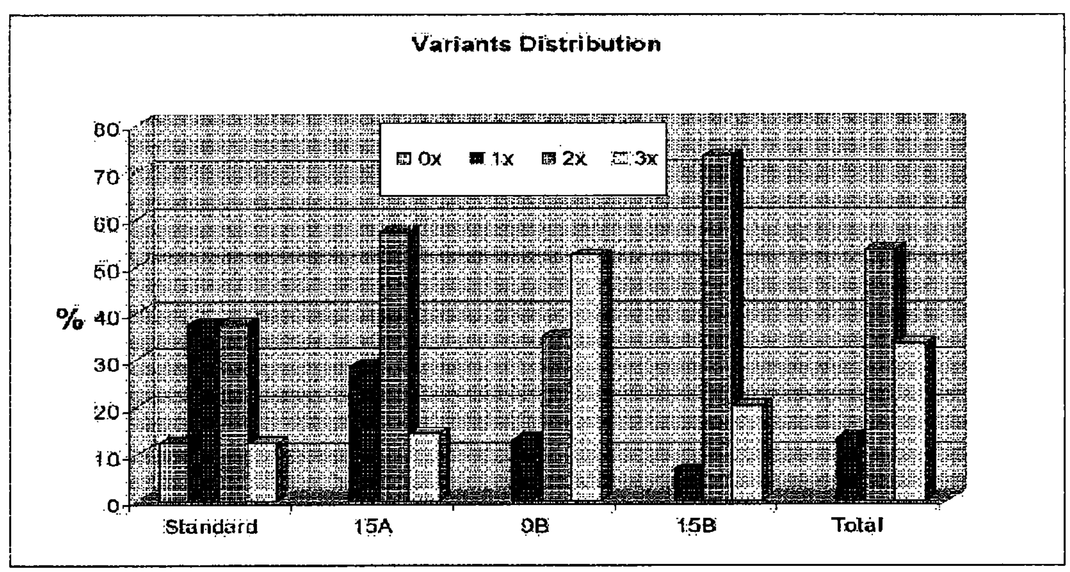
FIG. 12. Distribution of possible combinations with three mutation sites. Standard: calculated variant distribution under ideal situation; 15A: reaction condition 3 with *E. coli* strain XL1-Blue; 9B: reaction condition 2 with *E. coli* strain Stbl2; 15B: reaction condition 3 with *E. coli* strain Stbl2; Total: data combined from 15A, 9B and 15B; Ox: no mutation; 1×: single mutation; 2×: two mutations; 3×: three mutations.

In the third experiment, three sites on a gene were chosen to be combined (FIG. 11). The reactions were set up using forward primers on two sites and one reverse primer on the third site. The variants from the reactions were identified by sequencing. In this case, there were eight different possible combinations. Under 9B condition, all 8 variants were recovered by sequencing 24 clones. See FIG. 12.

Example 5

Figure 13:
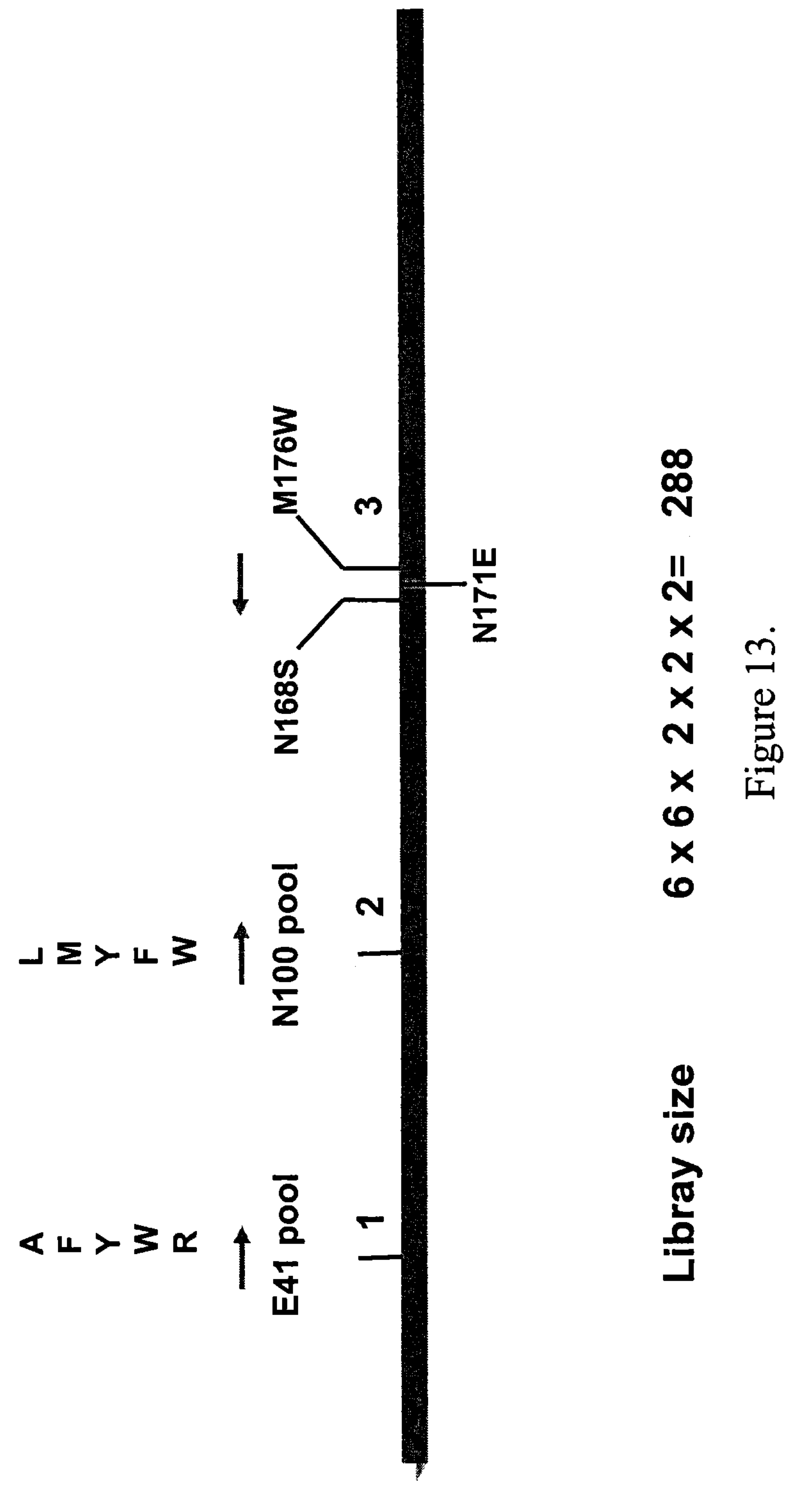
FIG. 13. A map of primers annealing with 5 mutation sites and 13 mutants.
Figure 14A:
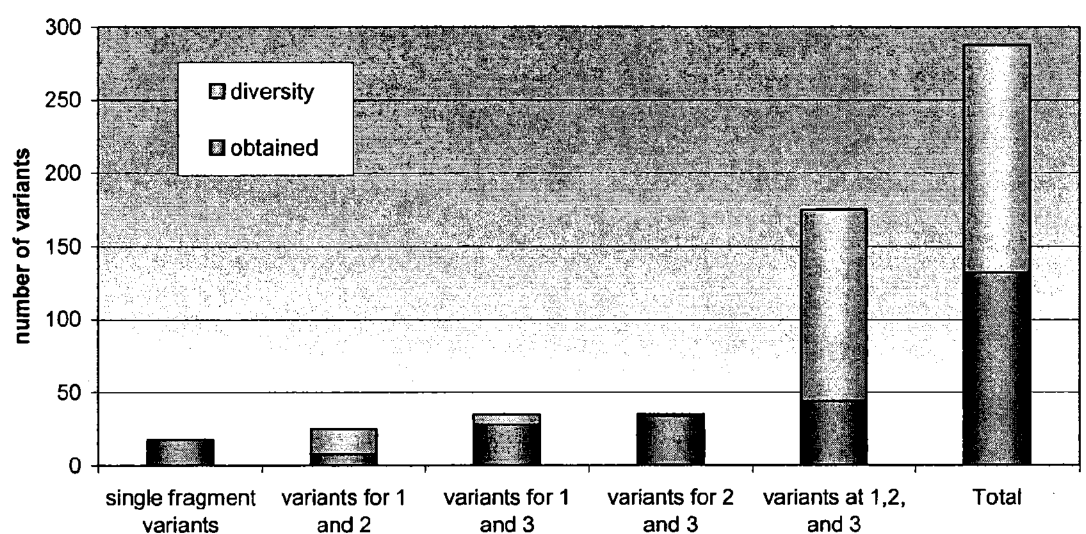
FIG. 14 A, B, C. Unique variant combinations in five mutation sites and 13 primers assembly. Breakdown of variants in TMCA round I (A), after round II (B), a map of primers annealing (C).
Figure 14B:
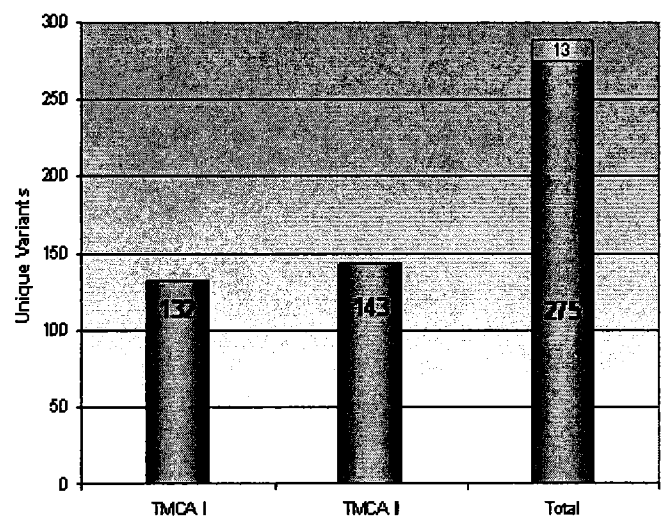
Figure 14C:
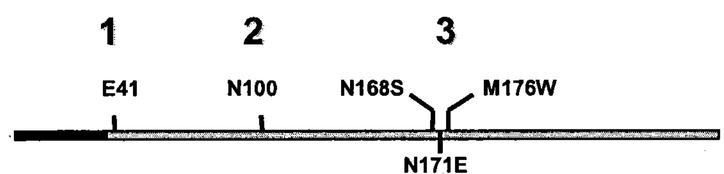

13 GSSM$^{SM}$ up-mutants were selected (5 sites) to improve thermal stability and increase specific activity of lipase (FIG. 13). Three sites (N168S, N171E, and M176W) were grouped together and were contained in one primer. The library size was 6×6×2×2×2=288. The reactions were set by the following method: the forward primers were grouped into a forward group and the reverse primers were grouped into a reverse group, and the primers in the forward group and the primers in the reverse group, independently of one another, were normalized to be equal concentration in the corresponding group regardless of positions on the template polynucleotide, and wherein after the normalization an equal amount of the forward and reverse primers was added to the reaction. The combination of positions 1 and 2 was biased (FIGS. 13 and 14A, B, C). A lower percentage of the possible unique variants were achieved for combinations of positions 1 and 2 compared with combinations of positions of 1 and 3 or positions 2 and 3. Two rounds of the TMCA reaction have been performed. In Round II, some of the variants obtained from Round I were used. After sequencing 720 clones (2.5× coverage of the library), 46% of the 288 unique variants in Round I were obtained. A 1× coverage sequencing would mean that the number of variants (progeny) sequenced equals the number of possible unique variants, therefore, 2.5× coverage indicates that the number of variants (progeny) sequenced equals 2.5 times the possible number of unique variants (288). Two rounds of the TMCA reaction have been performed. In Round II, some of the variants obtained from Round I were used as template polynucleotides. The primers used for each TMCA reaction in Round II were tailored to obtain variants not achieved in Round I. After Round II, 95.5% of the 288 unique variants were obtained. Ten up-mutants were obtained from this library after screening (FIG. 14A, B, C).

The Examples show that the TMCA method allows making combinatorial libraries efficiently. Some limitations are defined by mutant positions but alternatives can be designed to overcome these limitations. The new improved modification significantly reduce bias. Multiple rounds of the TMCA reaction can be performed to overcome some bias. The TMCA method is shown to be effective for multiple enzymes and vector systems. A vector size limitation may be as long as 11 kb.

Obviously, numerous modifications and variations of the present invention are possible in light of the above teachings. It is therefore to be understood that within the scope of the appended claims, the invention may be practiced otherwise than as specifically described herein.

The invention claimed is:

1. A method of producing a plurality of modified polynucleotides having more than one mutation per polynucleotide, comprising: (a) adding at least three primers to a double stranded template polynucleotide in a single reaction mixture, wherein the at least three primers are not overlapping, and wherein each of the at least three primers comprise at least one mutation different from the other primers, wherein at least one primer is a forward primer that can anneal to a minus strand of the template and at least one primer is a reverse primer that can anneal to a plus strand of the template, and (b) subjecting the reaction mixture to a polymerase extension reaction to yield a plurality of extended modified polynucleotides having more than one mutation per polynucleotide from the at least three primers; wherein the modified polynucleotides comprise all possible combinations of mutations to the template polynucleotide.

2. The method of claim 1, further comprising transforming a cell with the plurality of extended products that have not been treated with a ligase.

3. The method of claim 2, further comprising recovering the plurality of extended modified polynucleotides from the cell.

4. The method of claim 3, further comprising analyzing the plurality of extended modified polynucleotides.

5. The method of claim 4, wherein analyzing comprises expressing at least one of the plurality of extended modified polynucleotides and analyzing the polypeptide expressed therefrom.

6. The method of claim 5, further comprising selecting the plurality of extended modified polynucleotides comprising the mutations of interest.

7. The method of claim 1, further comprising before step (a) obtaining sequence information of the template polynucleotide, and identifying three or more mutations of interest along the template polynucleotide.

8. The method of claim 1, further comprising analyzing the plurality of extended modified polynucleotides produced by the polymerase extension.

9. The method of claim 1, further comprising treating the plurality of extended modified polynucleotides with an enzyme, thereby destroying the template polynucleotide, transforming the treated extended modified polynucleotides into a cell, recovering the plurality of extended modified polynucleotides from the cell, and selecting the plurality of extended modified polynucleotides comprising the mutations of interest.

10. The method of claim 9, wherein the cell is an *E. coli* cell.

11. The method of claim 9, wherein the enzyme is a restriction enzyme.

12. The method of claim 11, wherein the restriction enzyme is the DpnI restriction enzyme and the cell is an *E. coli* cell.

13. The method of claim 1, wherein at least four primers are added.

14. The method of claim 1, wherein at least five primers are added.

15. The method of claim 1, wherein at least six primers are added.

16. The method of claim 1, wherein at least eight primers are added.

17. The method of claim 1, wherein at least twelve primers are added.

18. The method of claim 1, wherein each primer comprises a single point mutation.

19. The method of claim 1, wherein at least two forward primers comprise a different change in the same position on the template polynucleotide.

20. The method of claim 1, wherein at least two reverse primers comprise a different change in the same position on the template polynucleotide.

21. The method of claim 1, wherein at least one primer comprises at least two changes in different positions on the template polynucleotide.

22. The method of claim 1, wherein at least one primer comprises at least two changes in different positions and at least two forward or two reverse primers comprise a different change in the same position on the template polynucleotide.

23. The method of claim 1, wherein the at least one mutation is selected from the group consisting of a change in one or more nucleotide or encoded amino acid sequences, an insertion, and a deletion.

24. The method of claim 1, wherein the template polynucleotide is a circular double-stranded DNA.

25. The method of claim 1, wherein at least one primer is a set of degenerate primers each comprising a degenerate position, wherein the mutation of interest is a range of different nucleotides at the degenerate position.

26. The method of claim 1, wherein at least one primer is a set of degenerate primers comprising at least one degenerate codon corresponding to at least one codon of the template polynucleotide and at least one adjacent sequence that is homologous to a sequence adjacent to the codon of the template polynucleotide.

27. The method of claim 26, wherein the degenerated codon is N,N,N encoding a naturally occurring amino acid.

28. The method of claim 26, wherein the degenerated codon can encode less than 20 naturally occurring amino acids.

29. The method of claim 1, wherein the forward primers are grouped into a forward group and the reverse primers are grouped into a reverse group, and the primers in the forward group and the primers in the reverse group, independently from one another, are normalized to be equal concentration in the corresponding group regardless of positions on the template polynucleotide, and wherein after the normalization an equal amount of the forward and reverse primers is added to the reaction.

30. The method of claim 1, further comprising before step (b): organizing the primers into multiple groups depending on their location on the template polynucleotide, wherein the primers covering the same selected region on the template are in one group, normalizing the grouped primers within each group to be equal concentration, pooling the forward primers within one group into a forward group and normalizing concentration between each group of the forward primers to be equal, pooling the reverse primers within one group into a reverse group and normalizing concentration between each group of the reverse primers to be equal, and adding an equal amount of the pooled forward and reversed primers into the reaction.

31. The method of claim 1, further comprising performing two rounds of steps (a) to (b), and using polynucleotides produced in the first round as the template polynucleotide in the second round.

32. A method of producing a plurality of modified polynucleotides comprising mutations of interest wherein the polynucleotides comprise more than one mutation per polynucleotide, comprising: (a) adding at least two primers to a double stranded template polynucleotide in a single reaction mixture, wherein the at least two primers are not overlapping, and wherein each of the at least two primers comprise at least one mutation different from the other primer(s), wherein at least one primer is a forward primer that can anneal to a minus strand of the template and at least one primer is a reverse primer that can anneal to a plus strand of the template, (b) subjecting the reaction mixture to a polymerase extension reaction to yield a plurality of extended modified polynucleotides from the at least two primers, wherein the plurality of extended modified polynucleotides comprise at least two or more mutations in codons for at least two or more different amino acids, (c) treating the plurality of extended modified polynucleotides with an enzyme, thereby destroying the template polynucleotide, (d) transforming the treated extended modified polynucleotides that have not been treated with a ligase into a cell, (e) recovering the plurality of extended modified polynucleotides from the cell, and (f) selecting the plurality of extended modified polynucleotides comprising the mutations of interest wherein the polynucleotides comprise more than one mutation per polynucleotide, wherein the modified polynucleotides comprise all possible combinations of mutations to the template polynucleotide.

33. A method of producing a plurality of modified polynucleotides having more than one mutation per polynucleotide, comprising: (a) adding at least three primers to a double stranded template polynucleotide in a single reaction mixture, wherein the at least three primers are not overlapping, wherein each of the at least three primers comprise at least one mutation different from the other primers, wherein at least one primer is a forward primer that can anneal to a minus strand of the template and at least one primer is a reverse primer that can anneal to a plus strand of the template, and wherein the forward primers are grouped into a forward group and the reverse primers are grouped into a reverse group, and the primers in the forward group and the primers in the reverse group, independently from one another, are normalized to be equal concentration in the corresponding group regardless of positions on the template polynucleotide, and wherein after the normalization an equal amount of the forward and reverse primers is added to the reaction and (b) subjecting the reaction mixture to a polymerase extension reaction to yield a plurality of extended modified polynucleotides having at least two or more mutations in codons for at least two or more different amino acids, wherein the modified polynucleotides comprise all possible combinations of mutations to the template polynucleotide.

* * * * *